(12) United States Patent
Vetter et al.

(10) Patent No.: US 8,920,646 B2
(45) Date of Patent: Dec. 30, 2014

(54) CHROMATOGRAPHY COLUMN

(75) Inventors: Udo Johannes Vetter, Ravensburg (DE);
Jürgen Friedle, Stuttgart (DE);
Manfred Strittmatter, Fronreute-Staig (DE); Lothar Britsch, Reute/Freiburg (DE)

(73) Assignee: ATOLL GmbH, Weingarten (DE)

( * ) Notice: Subject to any disclaimer, the term of this patent is extended or adjusted under 35 U.S.C. 154(b) by 1677 days.

(21) Appl. No.: 11/918,928

(22) PCT Filed: Apr. 21, 2006

(86) PCT No.: PCT/EP2006/003663
§ 371 (c)(1),
(2), (4) Date: Oct. 19, 2007

(87) PCT Pub. No.: WO2006/111397
PCT Pub. Date: Oct. 26, 2006

(65) Prior Publication Data
US 2009/0065415 A1 Mar. 12, 2009

(30) Foreign Application Priority Data

Apr. 21, 2005 (DE) .......................... 10 2005 019 703

(51) Int. Cl.
*G01N 30/60* (2006.01)
(52) U.S. Cl.
CPC .................................... *G01N 30/603* (2013.01)
USPC ........................................ 210/198.2; 210/656
(58) Field of Classification Search
CPC ................................................... G01N 30/603
USPC ................. 210/198.2, 635, 656, 659
See application file for complete search history.

(56) References Cited

U.S. PATENT DOCUMENTS

| 3,487,938 A | * | 1/1970 | Patterson | 210/198.2 |
|---|---|---|---|---|
| 3,511,377 A | * | 5/1970 | Hrdina | 210/198.2 |
| 3,878,099 A | * | 4/1975 | Ogle | 210/198.2 |
| 4,283,280 A | * | 8/1981 | Brownlee | 210/198.2 |
| 4,309,286 A | * | 1/1982 | Lenihan et al. | 210/198.2 |
| 4,865,728 A | * | 9/1989 | Larsson | 210/198.2 |
| 4,888,112 A | * | 12/1989 | Kronwald | 210/198.2 |
| 5,167,810 A | * | 12/1992 | Vassarotti et al. | 210/198.2 |

(Continued)

FOREIGN PATENT DOCUMENTS

| DE | 44 07 889 A1 | 9/1995 |
|---|---|---|
| EP | 0 671 624 B1 | 9/1995 |

(Continued)

OTHER PUBLICATIONS

Snyder (Introduction to Modern Liquid Chromatography, 1979, pp. 204-206.*

(Continued)

*Primary Examiner* — Ernest G Therkorn
(74) *Attorney, Agent, or Firm* — Harness, Dickey & Pierce, P.L.C.

(57) ABSTRACT

Disclosed is a chromatographic column for use with chromatographic materials packed in a defined manner.
Said chromatographic column is characterized in that the chromatographic material in a defined compressed state is enclosed in a column body (1), which is preferably cylindrical and is provided with a discharge opening (9), between two filter plates which are fixed at a specified distance from one another by contact with support surfaces situated inside the column body.

26 Claims, 11 Drawing Sheets

(56) References Cited

U.S. PATENT DOCUMENTS

| | | | |
|---|---|---|---|
| 5,169,522 A * | 12/1992 | Shalon et al. | 210/198.2 |
| 5,186,839 A * | 2/1993 | Kimura et al. | 210/656 |
| 5,188,730 A * | 2/1993 | Kronwald | 210/198.2 |
| 5,194,225 A * | 3/1993 | Muller et al. | 422/70 |
| 5,238,556 A * | 8/1993 | Shirkhan | 210/198.2 |
| 5,336,412 A * | 8/1994 | Huse et al. | 210/635 |
| 5,378,361 A * | 1/1995 | Baeckstrum | 210/198.2 |
| 5,693,223 A * | 12/1997 | Yamada et al. | 210/198.2 |
| 5,811,665 A * | 9/1998 | Gregor et al. | 73/61.53 |
| 6,171,502 B1 * | 1/2001 | Mueller et al. | 210/656 |
| 6,177,008 B1 * | 1/2001 | Treiber et al. | 210/198.2 |
| 6,398,953 B1 * | 6/2002 | Hargro | 210/198.2 |
| 6,444,122 B1 * | 9/2002 | Van Davelaar | 210/198.2 |
| 6,565,745 B2 * | 5/2003 | Hodgin et al. | 210/198.2 |
| 6,783,673 B2 * | 8/2004 | Horsman et al. | 210/198.2 |
| 6,802,968 B2 * | 10/2004 | Leavesley et al. | 210/198.2 |
| 6,811,688 B1 * | 11/2004 | Hofmann | 210/198.2 |
| 7,727,402 B2 * | 6/2010 | Cummings | 210/656 |
| 2007/0114163 A1 * | 5/2007 | Cummings | 210/198.2 |

FOREIGN PATENT DOCUMENTS

| | | |
|---|---|---|
| JP | 2004/283647 A | 10/2004 |
| JP | 2004283647 | 10/2004 |
| WO | 02/053256 A | 7/2002 |
| WO | 02/053256 A1 | 7/2002 |

OTHER PUBLICATIONS

Patent Abstracts of Japan vol. 2003, No. 12, Dec. 5, 2003.

* cited by examiner

CHROMATOGRAPHY COLUMN

CROSS-REFERENCE TO RELATED APPLICATIONS

This application is a 371 National Stage of International application No. PCT/EP2006/003663, filed Apr. 21, 2006. This application claims the benefit of DE 10 2005 019 703.5, filed Apr. 21, 2005. The disclosure(s) of the above applications are incorporated herein by reference.

TECHNICAL FIELD

A miniature chromatographic column is disclosed in which a permanently defined compression of a chromatographic material enclosed between two filter plates is achieved by means of a plunger inserted into the column which fixes the upper filter plate in place, and which is provided with an opening of a suitable size with respect to the filter plate. By means of a multiple holding device large numbers of the columns may be used for simultaneous processing of an equivalent number of chemical or biological samples, or in applications involving stepwise elution. The flow in the columns is created by either gravitational force or centrifugal force, or a combination of both.

PRIOR ART (BACKGROUND OF THE INVENTION)

Chromatographic separations of chemical or biological substance mixtures in liquid samples on chromatographic materials are usually carried out using columns in which the compressed packing of these materials is fixed by an adapter which may be stationarily set in position in the column tube.

The chromatographic materials may be elastic, quasi-elastic, or nonelastic. When nonelastic materials are used, after a certain period of time a defined packing of the material results inside the column due to sedimentation. Thus, it is not absolutely necessary to achieve physical compression of the chromatographic material upon insertion of the plunger.

The need for fixing the height and thickness of the packing results from the elastic behavior of certain chromatographic materials during packing under flow. As the result of sedimentation from homogeneous suspension, in particular highly porous carrier materials such as the known carbohydrate-or polymer-based gel-like matrices, for example Sepharose®, Toyopearl®, Fractogel®, Fractoprep®, Macroprep®, Unosphere®, and others, in addition to derivatives obtained from chemical surface modification, occupy a volume during the packing process which is dependent on the duration and linear flow rate. The packing pressure is ultimately the determining variable for the onset of compression of the gel. However, as soon as this pressure acting on the packed gel is discontinued, the elasticity of the packing becomes noticeable, such that an initially rapid and then slower expansion of the packed gel sediment occurs. This expansion comes to a standstill when the sedimenting effect of gravity is in equilibrium with the expansion pressure. As a rule, the volume resulting from the expansion of a gel suspension previously compressed under flow does not completely correspond to the volume obtained from the same quantity of gel as the result of sedimentation under the force of gravity.

Since the pressure drop over a given gel packing is a complex function of the linear flow rate, the viscosity of the eluent, the temperature, and other parameters, a characteristic compression results for gel packings operated in open mode, which in addition does not remain constant during a chromatographic separation. However, a fixed, defined packing density is absolutely essential for achieving reproducible results in chromatographic separations. For this reason, chromatographic columns to be filled with quasi-elastic carrier materials to a variably specified height are preferably equipped with adapters which seal the packing and which may be held in a defined position by mechanical locking, regardless of the pressure drop in the column. Such adapters generally require a complex design and contribute significantly to high manufacturing costs, in particular for small-volume columns. In another embodiment of such columns, the option of specifying an adjustable height of the gel packing is omitted in favor of a simpler design. A stationary end piece is used which a priori allows only a single specified bed height of the gel packing. For such columns, a particular difficulty of the packing procedure is closing off the column in the packed state of the chromatographic material without elastically re-expanding the gel in the process.

For operation, both types of columns are generally connected to a pump which delivers the eluent at a suitable flow rate and is able to overcome the pressure drop over the column. These columns must therefore be operated sequentially, even for small volumes of packed chromatographic material. In contrast, simultaneous operation of multiple columns requires the use of a corresponding number of pump systems, which entails a very complex equipment setup.

Specifically in the biological sciences, however, there is frequently a need for processing of numerous small-volume samples in chromatographic separation steps as simultaneously as possible. To solve the dilemma of either a high expenditure of time for sequential separations or the tremendous complexity of equipment for the simultaneous use of multiple chromatographic systems, various solutions have been developed in the past for which, however, either the actual chromatographic separation step is reduced to simple sequences of adsorption and desorption, or eluent no longer passes through the chromatographic medium in the sense of classical chromatographic columns. Therefore, these technical solutions for simultaneous separation of multiple samples do not permit separation results of a quality known to one skilled in the art from the classical chromatographic columns. This relates in particular to the achievable number of theoretical plates and to the asymmetry of the sample distribution in the chromatographic material. Mentioned as examples are "spin columns" (columns for centrifugation) and devices for carrying out batch adsorption (adsorption from a homogeneous suspension) in parallel using numerous samples. Spin columns, as disclosed in U.S. Pat. No. 6,103,195, for example, contain the particular chromatographic material as a filter cake, in a manner of speaking, which is held in the column by means of a filter plate. After it is loaded, sample liquid or eluent is caused to flow through the chromatographic material by centrifugation. Firstly, the chromatographic material, if it is one of the above-referenced quasi-elastic gels, is not present in a defined compressed packing. Secondly, the flow of eluent through the chromatographic material is basically asymmetrical in the centrifugal field, since, even in the most favorable case of a centrosymmetrical configuration of the column, the centrifugal force defines a right angle with respect to the path velocity only for the center longitudinal axis of the column, and for all other locations on the column cross section defines a different angle. As a result of the high mobility of the liquids applied, the chromatographic material has a nonuniform sample loading, and the subsequent elution also occurs in a nonuniform manner.

In other embodiments of columns which are to be operated simultaneously in large numbers without connection to pump systems, a uniform flow of the eluent through a usually cylindrical packing of chromatographic material occurs by the simultaneous application of vacuum to the discharge outlets of the columns. For this purpose, standardized systems of columns in the form of 96-well microtiter or filter plates are primarily used. Here as well, the chromatographic materials used are not present in a defined packed form. In addition, these systems are less well suited for applications involving proteins and other high-molecular biological substances, since after a period of time air or other gas passes through the chromatographic material. Although residual interstitial liquid may be removed from the chromatographic material by additional centrifugation, due to variable flow rates in vacuum operation in individual columns it is not possible to achieve uniform conditions for the separation processes. A further disadvantage of vacuum-operated multicolumn systems is the potential denaturing of proteins resulting from the formation of foam when the sample exits the chromatographic material, since the partial vacuum is particularly strong at this location.

One of the simplest options for simultaneously carrying out multiple chromatographic separations for biological water-soluble substances is the use of open gravity-operated columns. Such columns are available in many designs from numerous suppliers, and are provided for various purposes. Examples include the products Econo-Pac® columns or Poly-Prep® ion exchange columns (Bio-Rad Laboratories, Inc., Hercules, Calif., USA) or Mobius® plasmid kits (Merck Biosciences GmbH, Schwalbach, Germany). These columns generally operate by means of gravity-driven stepwise elution, and allow true chromatographic separations to be carried out. However, in this case as well the chromatographic media are present only in a low packing density as a result of sedimentation of the gel particles under the flow rate induced by gravity. Thus, the efficiency of the separation media used, primarily with respect to the achievable plate number, is not fully utilized.

Separations carried out simultaneously in batch mode, i.e., by adsorption onto the separation medium from a homogeneous suspension and subsequent desorption, represent the simplest technique for simultaneous use of various chromatographic media with numerous samples. In principle, this technique only offers a separation efficiency which corresponds to one theoretical plate per separation step. The seamless continuity of successive settings of the adsorption equilibrium, such as that in a chromatographic column, is not provided. A further disadvantage of the batch method is the residual liquid in the intraporous volume of the separation medium in each step of the separation from supernatant, regardless of which method (decantation, filtration, etc.) is used for the separation. This intraporous liquid still contains all of the dissolved substances in the same concentrations as in the preceding work step, and thus transfers these to the subsequent step. In principle, therefore, in batch mode a result which corresponds to the chromatographic separation efficiency in columns is achievable only for a very large number of consecutively staged adsorption and desorption steps. Use of this method is therefore limited by obvious practical considerations.

From the standpoint of chromatographic separation efficiency, the technical solutions discussed have the disadvantage either that they may be parallelized only with a high expenditure of time and complexity of equipment, or that the chromatographic separation efficiency of the separation media cannot be fully utilized in the absence of sufficient and permanent compression of the media. The latter-referenced drawback in particular could be partially or completely eliminated by designing gravity-operated columns in which the chromatographic media are present with sufficiently dense packing. One skilled in the art is aware that as the compression increases in such a packing with the maximum possible homogeneity, such as that of bead-shaped microparticles, the volume present between the particles becomes smaller, thereby increasing the theoretical plate number of this packing in chromatographic separations. Thus, for a given separation medium the maximum plate number is achieved for a very specific optimal compression.

The technical object to be achieved, therefore, is to construct a chromatographic column having a simple design in such a way that for a uniform geometry of the column packing, various chromatographic media may be packed in the column at the respective optimal permanent compression. A further aim is to be able to simultaneously operate large numbers of the affected columns, under gravity alone or with a combination of the influence of gravity and centrifugal force, in applications involving stepwise elution. The affected columns may characteristically be manufactured economically in miniaturized form, and in their design for parallel use are compatible with existing laboratory robotic systems.

DETAILED DESCRIPTION WITH EXAMPLES

Figure 1:
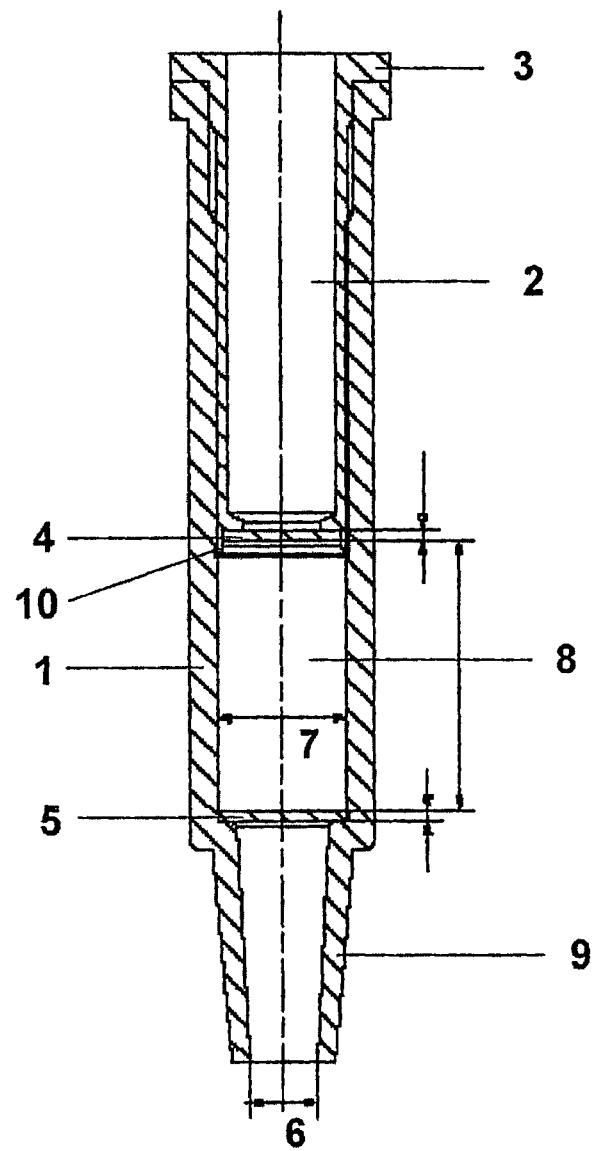
FIG. 1 is a cross-sectional view of a chromatography column in accordance with the present teachings.

The described technical object is achieved by enclosing a quasi-elastic chromatographic medium in a cylindrical chromatographic column between two filter plates of sufficient mechanical stability, such that the lower filter plate rests with its outer edge on a circular support integrated into the column, and the upper filter plate is permanently held in position, bordering the compressed chromatographic medium from above, by a sample reservoir with a lower central opening which is fabricated to fit exactly when inserted into the column. The upper filter plate may be integrated into the lower portion of the sample reservoir. Instead of a sample reservoir, also referred to as a sample chamber, a plunger may also be used. However, it is particularly advantageous to design same as a sample reservoir or to replace same with a sample reservoir due to the particularly compact design which may be achieved for the chromatographic column.

The porosity of the filter plates is selected with respect to the particle size distribution of the chromatographic materials used so that the smallest particles thereof are reliably retained by the filter plates. When deep-bed filters are used, for example for a chromatographic material having a particle size distribution of 40-90 mm, filter plates having a porosity of up to 25 µm are used. The filter plates may be composed of any suitable material known to one skilled in the art, such as polypropylene, polypropylene-polyethylene mixed polymer, polytetrafluoroethylene, cellulose, etc. The thickness of the filter plates is selected so that when used in the chromatographic column according to the invention the filter plates withstand the pressure, of the compressed chromatographic material without distortion of the planar shape. Filter plates made of polypropylene-polyethylene mixed polymer and having a thickness of 0.45 mm, for example for use with chromatographic materials such as Fractogel® (M) or Sepharose® FF or Sepharose® XL at 20% compression in the chromatographic columns according to the invention with an inner diameter of 5 mm, have been proven to have sufficient mechanical stability. For columns with inner diameters greater than 5 mm, correspondingly thicker filter plates are used, for example, a filter plate 1 mm thick for an inner diameter of 10 mm.

After the calculated volume of a set suspension of a chromatographic medium has been loaded into the column body, the defined permanent and product-specific compression of the chromatographic medium is achieved by uniformly compressing the chromatographic medium precisely to the predetermined volume upon subsequent insertion of the plunger or sample reservoir, including the upper filter plate. The outer diameter of the plunger or sample reservoir is selected in relation to the inner diameter of the column such that after insertion into the column to a depth specified by a check ring, the plunger or sample reservoir permanently remains in this position, also in opposition to the elastic restoring forces of the compressed chromatographic media which are directed against the upper filter plate. If the dimensions of the column and its individual parts have been suitably selected, despite compression by 20%, for example, in comparison to the volume obtained from the same quantity of chromatographic material after sedimentation under gravity, the above-mentioned quasi-elastic chromatographic materials may be operated under the force of gravity after filling the sample reservoir with liquid. It is advantageously possible to initiate the longitudinal gravity-driven flow in such upright columns by short-term centrifugation of the columns without noticeable efficiency-reducing asymmetries in the flow distribution occurring in the column.

It is noted here that the columns according to the invention are preferably loaded with quasi-elastic chromatographic materials. However, nonelastic chromatographic materials may also be introduced. A defined packing is obtained even when these materials are used. Insertion of the plunger or sample chamber requires no physical compression of the chromatographic material beyond the packing density, resulting solely from sedimentation, of a packing of the same quantity of chromatographic material. When either quasi-elastic or elastic chromatographic materials are used, insertion and lowering of the plunger or sample chamber until the stop in the column body is reached causes rapid displacement of liquid from the suspension of chromatographic materials, which preferably include particles, which has just been previously loaded in the column body. The average distance between these particles is thus reduced within a few seconds in the same manner as that achieved in the prior art by the outwardly forced flow of a suitable eluent from top to bottom in the direction of the column axis.

For the chromatographic column described herein, the "classification" of the generally differently sized particles of the chromatographic material, which otherwise would occur as a result of the different sedimentation velocity of these particles, is effectively prevented. This results in an essentially homogeneous distribution of the various particle sizes in the packing of the chromatographic material, i.e., the homogeneous packing required for chromatographic applications. The production of the compressed packing thus corresponds, in a manner of speaking, to a greatly accelerated sedimentation process in which there is no time for the particles to form nonhomogeneous size distributions. Hence, larger particles cannot sediment more quickly than small particles of the same density, which otherwise would be the case. This applies for all particleized chromatographic materials which for production reasons are composed of differently sized particles, i.e., which have a particle distribution range. In contrast, for packing of monodisperse chromatographic materials the factor of accelerated compression plays no special role. In this case, however, packings which are just as homogeneous are obtained by insertion of a plunger or sample chamber. Such chromatographic materials therefore require no special treatment. The majority of applicable chromatographic materials, however, are polydisperse with respect to particle size, so that the compression described here is particularly advantageous.

The principal distinction between elastic and quasi-elastic chromatographic materials on the one hand and nonelastic materials on the other hand is that in the latter the resulting sediment density is largely independent of the sedimentation velocity; i.e., during sedimentation the particles align in a spatially dense packing with the smallest possible interstitial volume. For the packing of these materials into the columns according to the invention, it is important only that the quantity of set suspension introduced into the columns corresponds to the desired packed volume. The filter plates provided in the chromatographic column thus represent only the liquid-permeable upper and lower closures for the particle packing and dictate the geometry thereof, in particular the desired entry and exit surfaces of the packing at right angles to the center axis of the chromatographic column.

Sedimentation of elastic and quasi-elastic chromatographic materials in no way results in the maximum packing density, but, rather, results in loose configurations of settled particles which do not have easily predictable total volumes. Many parameters influence the sedimentation characteristics. For example, the particles of the chromatographic materials themselves are more or less strongly elastically deformable. In addition, adhesive interactions between similar particles prevent the particles from settling into a maximally compressed packing.

The action of an external mechanical force on such a loose packing, preferably in the direction of the column axis, necessarily reduces the interspaces between the particles, with discharge of interstitial liquid, which is a condition for achieving good chromatographic separation efficiency. For greater compression, it is then increasingly possible for particles of the chromatographic material to become reversibly deformed, which may have a counterproductive effect.

It is therefore important to set the best relative compression as determined experimentally. When a force is exerted on the chromatographic material for this purpose, it has been shown that removing the force causing the compression permits a more or less rapid expansion of the compressed packing to a larger volume. In the case of ideal elasticity, the volume of a loose gravitational sediment would readjust. In practice, however, only a partial re-expansion is usually observed. Therefore, this is referred to as "pseudoelasticity" of the chromatographic material. This results in the necessity to keep compressed material in a precompressed state by use of mechanical, liquid-permeable barriers. This is easily achieved by means of the filter holders according to the invention described herein. This has proven satisfactory in particular for mini-columns, i.e., chromatographic columns having small dimensions, in particular small volumes.

For applications with small volumes of chromatographic media and substance samples to be separated, one particularly preferred embodiment of the novel column is illustrated as a drafting diagram in FIG. 1. The numbered parts and features are as follows: column body 1, sample chamber 2, sample chamber stop 3, upper filter plate 4, lower filter plate 5, discharge outlet diameter 6, gel chamber inner diameter 7, gel chamber 8, and discharge outlet 9 with outer dimensions according to Luer standards. The illustration shows the column without loaded chromatographic material and with an empty sample chamber. The individual parts of the column (column body and sample reservoir) may be fabricated on a lathe or also by injection molding. Polypropylene, polyethylene, polymethacrylate, polyethyl ether ketone, and polystyrene are examples of suitable production materials. However, other materials in the plastics and metals categories in addition to mixed forms thereof known to one skilled in the art may also be used. For applications in the field of chromatography of biological samples, inert plastic materials having the smoothest possible surface are preferred. Compared to manufacture from metals, the latter option also currently allows the most economical large-scale production of miniature columns.

The column body of the chromatographic column according to the invention comprises a straight cylinder having a profiled upper closure and a downwardly tapering discharge outlet at the lower end. Located inside the chromatographic column at the transition between the column tube and the discharge outlet is a support, in this case a circular support, for the lower filter plate, which rests thereon with an exact fit. The lower filter plate forms the lower closure of the gel chamber, and under all operating conditions represents an impermeable barrier for the particles of the chromatographic material packed in the gel chamber. The upper end of the gel chamber is closed off by the upper filter plate matched for a precise fit, which in the illustrated embodiment is inserted into the lower end of the plunger, which in this case is designed as a sample chamber. Similarly as for the lower filter plate, the upper filter plate is fixed in position by a circular support located at the lower end of the sample chamber. Thus, the position of the upper filter plate is also permanently fixed in place by the overall length of the sample chamber which is fully inserted into the column body. At the same time, this configuration of the filter plates fixes the height of the packing of the chromatographic material in the column. For inner column diameters of 3 mm to 10 mm, the mechanical stability of the 0.3-to 2-mm thick filter plates, which preferably are deep-bed filters made of polypropylene-polyethylene, polytetrafluoroethylene, or materials having similar properties, in conjunction with the filter supports ensures a secure enclosure of the packed chromatographic material in the gel chamber. The lower filter support should have a width of 0.2 to 2 mm, preferably 0.3 to 1 mm, particularly preferably 0.5 mm. The filter support on the lower end of the sample chamber should preferably have the same width as the lower filter support in the column body. However, the lower filter support may also have a width up to a value which leaves a central opening of at least 0.5 mm for the passage of liquid from the sample chamber. The sample chamber to be inserted into the column body is dimensioned in such a way that its inner volume which is available for accommodating samples or eluents is equal to or greater than the volume of the gel chamber.

The lower end of the plunger or sample chamber has a sealing lip, which when inserted into the column body ensures a peripherally sealing closure at the inner wall of the column body which seals off liquids. As a result, particles of the chromatographic material or liquid droplets adhering to the inner wall of the column body are completely entrained downward, together with the loaded suspension of the chromatographic material, until the specified height and compression of the packing thereof are achieved. This is the case when the plunger or sample chamber in its preferred embodiment is inserted into the column body until its upper stop meets the upper stop of the column body.

The advantage of providing the sample chamber with an upper stop is that the upper end of the assembled column has a seamless surface which reliably prevents accidental penetration of liquid or dust particles into the microgap between the column body and the sample chamber. A further advantage of the upper stop is that quick and precise final positioning of the sample chamber is greatly facilitated during assembly of large pieces of the chromatographic column according to the invention. Furthermore, the plunger, which in this case is designed as a sample chamber, has an outer diameter such that it is seated firmly in the column body after being completely introduced therein. This is achieved by selecting the outer diameter of the sample chamber to be 0.02 to 0.1 mm, preferably 0.03 to 0.05 mm, larger than the inner diameter of the column body.

As a result of the elastic properties of the materials used to manufacture at least one of these parts, application of force is necessary to insert the sample reservoir into the column body. Elastic deformation of this molded part or of both molded parts occurs, which results in a restoring force which in turn results in mutual fixing of these parts in their respective position. It has been observed that the sample reservoir remains in its position fixed in this manner, even when the gel chamber is loaded with compressed quasi-elastic chromatographic materials. In the case of polymethacrylate-based gels, for example, such as Toyopearl® 650 (M), the described design easily withstands compressions of up to 30% for several months without any noticeable change. The compression of the chromatographic materials refers to the reduced volume resulting from compression from a given volume of a sediment of these materials as the result of full sedimentation under the force of gravity. The volume of the sediment obtained under gravity is set at 100%.

The plunger inserted into the chromatographic column, which according to the previous discussions may also be designed as a sample chamber, is used as a filter holder. This filter holder operates in particular by the fact that, by means of a sealing lip and the filter plate used, i.e., by use of conventional parts, during insertion into the column body the filter holder displaces and entrains the chromatographic material, previously loaded in the form of a suspension, downward in an inwardly sealing manner against the column wall, i.e., downward in the direction of the lower filter plate. In contrast to known screw-in adapters, the chromatographic material is homogeneously compressed to a desired value within a few seconds without the necessity of an outwardly acting flow of a medium. This procedure allows a large number of columns to be easily and reproducibly packed with much less effort than for packing under flow.

The special feature of this technical solution lies in particular in the combination of the chromatographic column with a plunger or a sample chamber. The dimensions of the chromatographic column and of the filter holder are selected in such a way that the desired clamping characteristics are achieved. The plunger or sample chamber used as a filter holder is designed such that, after insertion into the chromatographic column, the tight contact between the outer wall of the filter holder and the inner wall of the column body effectively prevents the filter holder from sliding backward due to the elastic restoring force of the packing of the chromatographic material. Thus, the upper filter plate fixed by the filter holder is held in place from below by the compressed chromatographic material, and as a result of the firm seating of the filter holder on the stop in the column body is also acted on from above by a predefined force and is fixed in a predefined position. The filter holder is thus characterized in that it also withstands the pressure drop which occurs due to longitudinal transport of liquid through the column, and remains in a fixed position on account of contact pressure on the column wall.

Furthermore, it has been shown that the chromatographic columns according to the invention may essentially be operated under the force of gravity, using the above-referenced media with corresponding compressions and packed up to a height in the gel chamber between 2 and 25 mm, preferably between 5 and 20 mm, in particular between 8 and 12 mm. In other words, after the sample chamber of the upright columns is loaded with a liquid sample or an eluent, after a short time longitudinal flow results in the column, and the flow ceases precisely when the liquid level reaches the top edge of the upper filter plate. Optionally, the flow may be initiated immediately after loading the sample by briefly centrifuging for 5 to 15 seconds at a low centrifugal acceleration of 10 to 50 g. For columns having the dimensions illustrated in FIG. 1, centrifugation is preferably carried out for 10 seconds at 18 g, corresponding to an integral centrifugal acceleration of 5. Experience has shown that centrifugation steps using such low integral centrifugal accelerations have no apparent adverse effect on the separation efficiency of the chromatographic columns, since the predominant portion of the longitudinal liquid flow is additionally produced by gravity and is therefore uniform over the cross section of the column.

An important advantage of the chromatographic columns according to the invention is that a volume corresponding to the respectively loaded quantity of liquid always appears at the discharge outlet of the column. The dry running otherwise frequently observed in gravity operation of chromatographic columns is eliminated, since the liquid is prevented from dropping below the level of the upper filter plate due to the action of capillary forces in the filter plate. In addition, a possible subsequent centrifugation lasting up to 2 minutes, with accelerations up to 500 g, for removing liquid residues from the discharge outlets of the columns likewise does not result in dry running in the columns.

Applications

The chromatographic columns according to the invention may be used, individually or in numbers of up to several hundred simultaneously, in numerous applications for chromatographic separation of primarily biological substances, with elution in successive discrete work steps.

The following are examples of such applications:

Determination of the volumetric binding capacity and other characteristic properties of chromatographic materials for specific target substances under various conditions;

Optimization of parameters for the separation of biological substance mixtures;

Simulation of separation processes on a reduced scale, for example in process validation;

Various types of sample preparation for analytical or preparative purposes using biological samples, for example desalinization of protein solutions, separation of antibodies and albumins from blood samples, and isolation or purification of antibodies;

Purification of nucleic acids (plasmids, etc.) for various molecular biological and diagnostic purposes; and Purification of recombinant proteins provided with specific labeling by genetic engineering techniques (His-tag proteins, etc.).

Example 1

Figure 4A:
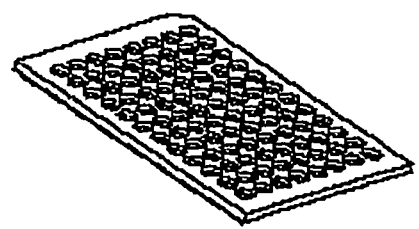
FIG. 4A is a perspective view of an exemplary design of a column holding plate.
Figure 4B:
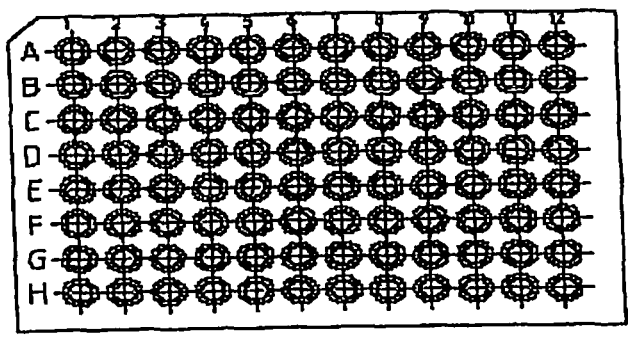
FIG. 4B is a top view of the column holding plate of FIG. 4A.
Figure 5:
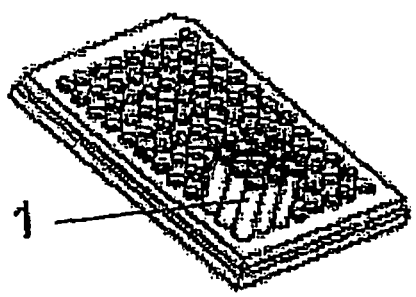
FIG. 5 is a perspective view of the column holding plate of FIG. 4A illustrated operatively associated with several chromatographic columns.

A total of 96 chromatographic columns according to the invention in the preferred embodiment according to FIG. 1, having a gel chamber inner diameter of 5 mm and a distance of 11 mm between the upper and lower filter plates, corresponding to a volume of the packed chromatographic material of approximately $216/\mu L$, and a total length of 38 mm were fitted with circular cutout filter plates by Freudenberg, model F02472. The thickness of the PP/PE filter plates was approximately 0.45 mm, and the average pore size was approximately $17 \mu m$. The upper filter integrated into the lower end of the sample chamber had a diameter of 4.65 mm, and the lower filter had a diameter of 5 mm. The filter plates were introduced into the separately provided column body and sample reservoir by use of a small insertion plunger of matching diameter. The column bodies were then placed symmetrically in rows of eight on two matching column holding plates having the dimensions of 96-well microtiter plates. FIG. 4A shows a perspective illustration of an exemplary design of a column holding plate, and FIG. 4B shows the top view. FIG. 5 shows a perspective illustration of an example of the column holding plate with several chromatrographic columns 1 placed thereon.

Using a multichannel pipette, 508 µL of a 1:1 suspension of Toyopearl® SuperQ 650 (M) in 1 M sodium chloride solution was added to each of the columns and allowed to settle for 5 minutes. The discharge opening of each column was then sealed, and the settled chromatographic material was compressed by inserting the sample reservoir to the bed height of 11 mm determined by the stop. The compression thus obtained was 15% relative to the volume of sedimented chromatographic material obtained by complete sedimentation of the same suspension under the force of gravity. The columns were equilibrated three times each with 180 µL 0.1 M sodium chloride solution. For this purpose the eluent was pipetted into the sample reservoir of each column, the columns on the column holding plates were centrifuged in a centrifuge having a swing-out rotor for microtiter plates (10 s, 300 rpm, corresponding to 18 g), and after standing for 3 minutes were recentrifuged (15 s, 500 rpm, corresponding to 50 g).

To test the separation efficiency of the minicolumns, the minicolumns were then each treated with 70 µL of a solution of vitamin $B_{12}$ in a 1 M sodium chloride solution. Centrifugation was performed immediately after the sample solution was loaded (10 s, 300 rpm, corresponding to 18 g). After standing for 3 minutes the samples in all the columns were uniformly pressed into the gel packing to a depth of approximately 5 mm on all sides. This was visually checked, since the columns were placed on the holding plate in rows at a distance from one another. At no time were appreciable boundary effects observed. The subsequent stepwise elution was carried out in the same manner as for the sample loading, except with 50 μL of the 0.1 M sodium chloride solution and a standing time of 5 minutes after the first centrifugation. The eluates were [placed] in UV microtiter plates (Greiner, UVStar® 96-well microplates). A separate microplate was used for each of the total of 6 elution steps.

each of the eluates was added 150 μL water, and the optical densities of the fractions were determined using a microplate photometer at 540 nm.

The results of the measurement of the optical density of the eluate fractions were represented in two-dimensional graphs, and a number of randomly selected data sets (20 out of 96) were subjected to computerized curve fitting. The best respective curve fit based on consistently meaningful functions was selected for the subsequent transfer to the graphical representation. This curve fit is referred to below as a pseudochromatogram.

The theoretical plate number (N, number per meter) and the asymmetry factor ($A_S$), parameters characterizing the pseudochromatogram, were determined in the same manner as for chromatograms plotted in the customary manner, corresponding to relationships (1) and (2):

$$N = 5.54 \times \left(\frac{V_e}{W_{1/2}}\right)^2 \times \frac{100}{BH} \quad (1)$$

$$A_s = \frac{B}{A} \quad (2)$$

where $V_e$=elution volume, $W_{1/2}$=width of the elution profile for half the maximum height, BH=bed height of the gel packing in cm, B and A=left and right section, respectively, of a parallel to the baseline at 10% maximum signal height, which is divided by a vertical connecting line to the maximum of the elution profile.

Results:

The measured values for each individual column were plotted in a diagram against the total associated volume eluted from this column up to that point. Computerized curve fitting was used to approximate elution profiles from these plots. For this purpose, equations of the general form

Figure 2:
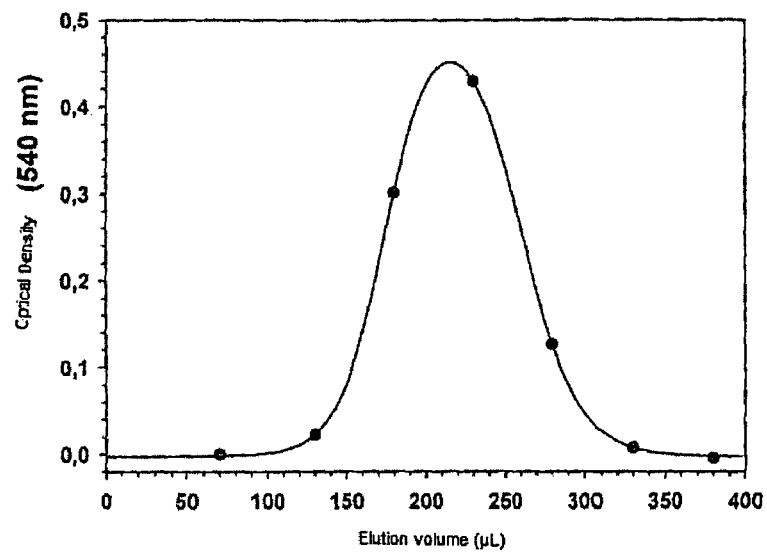
FIG. 2 is a chart of optical density versus elution volume for an exemplary column.

*In y=a+bx+cx²+dx³=ex⁴* or even higher orders of exponents were used. One example (column number 5) for an elution profile prepared in this manner is shown in FIG. 2. For this pseudochromatogram, 27 theoretical plates per cm and an asymmetry factor of 1.1 were determined.

Figure 3:
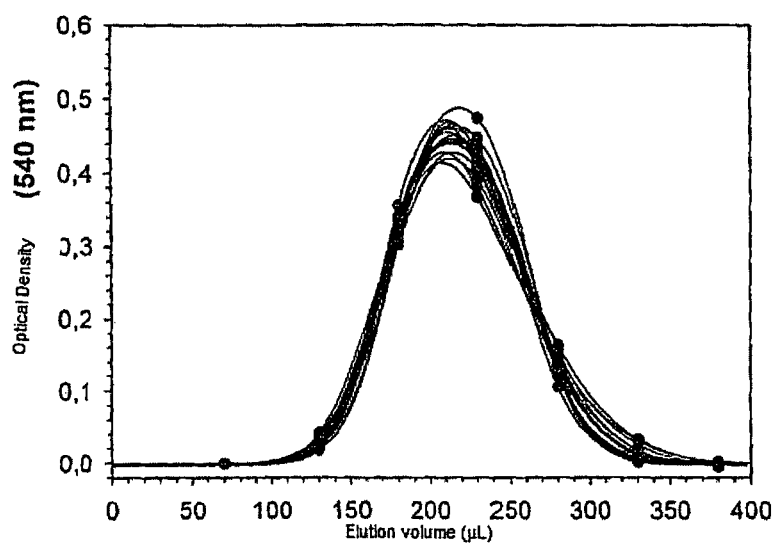
FIG. 3 is a chart of optical density versus elution volume for twenty random selected columns.

FIG. 3 shows a superimposition of the elution profiles of 20 randomly selected minicolumns out of 96. The graphical superimposition of the elution profiles shows that the individual minicolumns differ only slightly with regard to the asymmetry factor and plate number. The differences with respect to the maximum signal height (differences up to 0.1 OD) and in the speed of reaching the baseline on the ascending branch of the profiles (referred to as "tailing") may be seen. Differing characteristics in this range are also known for larger chromatographic columns. A summary of the numerical evaluation of the 20 selected columns is presented in Table 1. According to the table, the elution maxima were 214±3.2 μL, the number of theoretical plates was 24±2.2 per cm, and the asymmetry factor was 1.2±0.15, the maximum deviations from the mean being +4.8 and −8 μL for the elution maximum, +3 and −4 for the plate number, and +0.4 and −0.2 for the asymmetry factor.

It was found that for chromatographic columns having a conventional Luer adapter, also referred to as a Luer cone, liquid can be held in the attachment by capillary forces. The Luer adapter may also be replaced to counteract this phenomenon.

Figure 6:
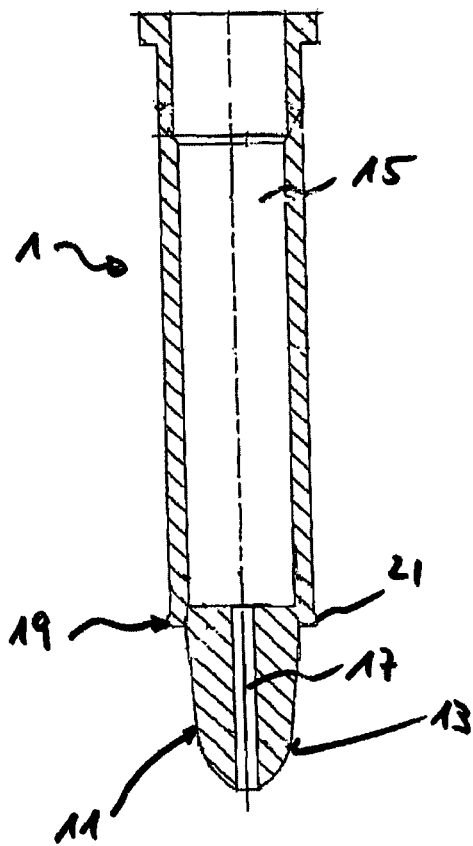
FIG. 6 is a cross-sectional view of a modified column body in accordance with the present teachings.

FIG. 6 shows a modified exemplary embodiment of a column body 1 which at its lower end is provided with a modified attachment 11 having a convexly curved, preferably parabolic, outer surface 13. A passage having the smallest possible internal diameter, preferably a capillary bore 17, runs in the attachment 11, preferably concentrically with respect to the center axis 15 of the column body 1. Liquid exiting this passage can adhere to the parabolic outer surface 15 only with great difficulty, so that in any event very small droplets cling to the lower opening of the capillary bore 17.

The column body 1 is preferably provided with a locking device 19 which securely holds the column body 1 in a sample plate. In the exemplary embodiment illustrated here, the locking device 19 includes at least one projection, preferably a circumferential annular bead 21, which makes a locking engagement in a suitable recess, in this case an annular recess, in the sample plate.

On the end of the column body 1 opposite from the Luer adapter according to FIG. 1, or on the end of the column body 1 opposite from the attachment 11 according to FIG. 6, a device may be provided which exerts a defined pressure force on the plunger inserted into the column body 1 or the sample chamber used at that location. In this manner a defined compression of the chromatographic material in the gel chamber 8 (see FIG. 1) may be established.

Figure 7:
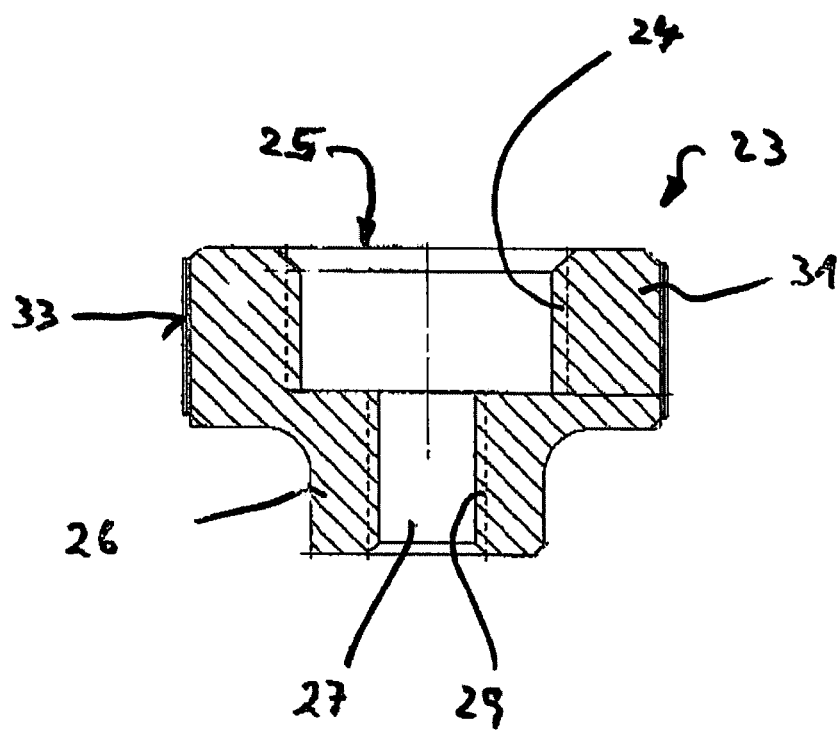
FIG. 7 is a cross-sectional view of an adapter element in accordance with the present teachings.

FIG. 7 shows an example of an adapter element 23 comprising a central opening 25 having an internal thread 24, and a cylindrical attachment 26 having a central recess 27 which likewise is provided with an internal thread 29. The outer diameter of the base body 31 in the region of the opening 25 is larger than in the region of the cylindrical attachment 26. The attachment is shown here with corrugation 33 on its exterior which increases the gripping capability of the adapter 23.

Figure 8:
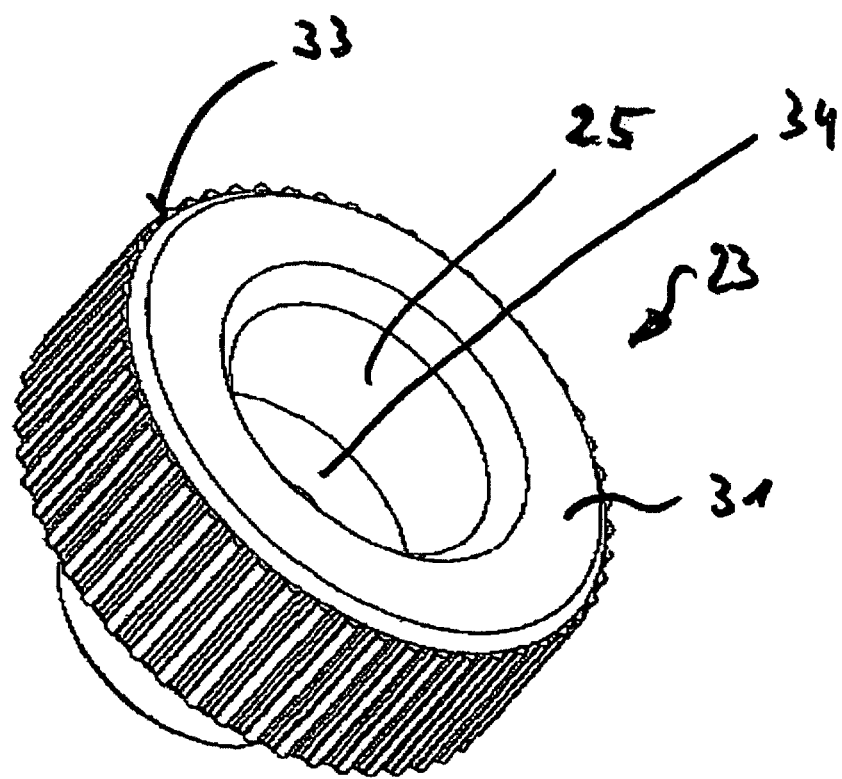
FIG. 8 is a perspective view of the adapter of FIG. 7.

FIG. 8 shows the adapter 23 in a perspective view in which the opening 25 may be clearly seen. The internal thread in this region is not shown in the illustration chosen here.

The figure clearly shows that in the region of the opening 25 the base body 31 is provided with corrugation 33 on its exterior, which may have extending bars and depressions in the longitudinal direction of the adapter 23. In principle, however, the gripping capability of the adapter 23 in this region may also be enhanced in other ways, such as by use of other structures or by coating with a gripping material.

The adapter 23 is screwed onto the rear end, i.e., the end of a column body 1 facing away from the Luer cone or attachment 11, the internal thread 24 cooperating with an external thread on the column body 1. Since the inner diameter of the recess 27 is smaller than the opening 25, this results in a base 34 for the opening 25 at this location which acts on a plunger, for example a sample chamber, or on an adapter which is inserted into the column body 1. When the adapter 23 is screwed more or less onto the column body 1, the base 34 increases the contact force more or less on the plunger or the adapter. When the adapter 23, in this case designed as an overlapping cover, is rotated the plunger or adapter is pushed more or less inside the column body 1, so that a desired compression of the chromatographic material in the gel chamber 8 may be set.

It is seen that the device enclosing the plunger 23 for setting the compression of the chromatographic material has a very simple design.

The internal thread 30 in the recess 29 of the adapter 23 is used to establish a connection for various media used when the chromatographic column is operated.

Figure 9:
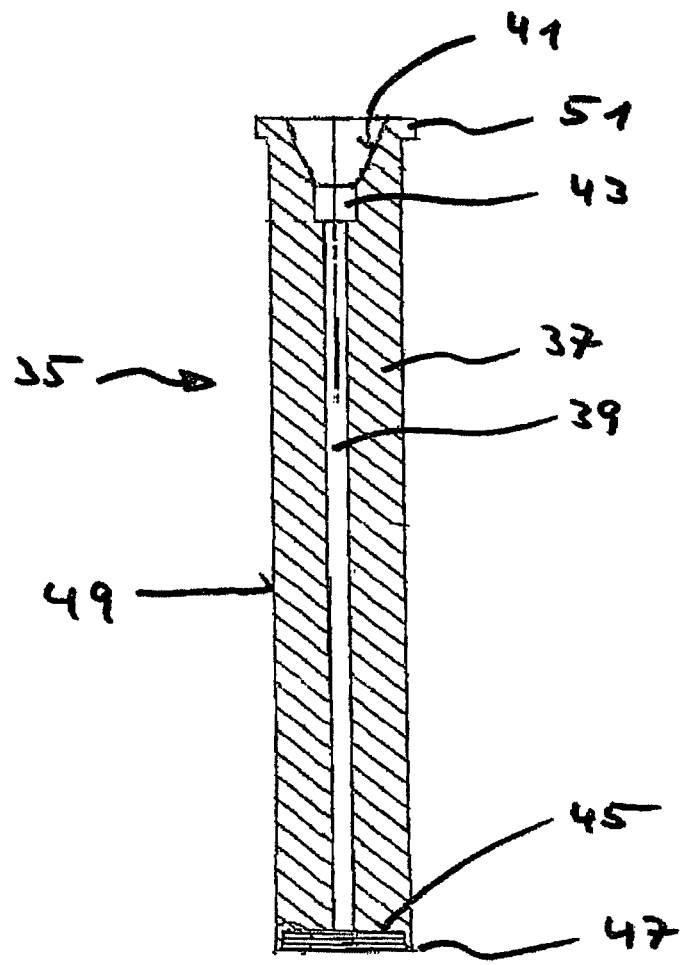
FIG. 9 is a cross-sectional view of a plunger in accordance with the present teachings.

In one preferred exemplary embodiment of a chromatographic column, instead of a sample chamber a plunger 35 designed as an adapter may be inserted inside the column body 1. FIG. 9 shows one preferred exemplary embodiment of such a plunger in the longitudinal section.

The illustrated plunger 35 has a base body 37 with a continuous opening of small diameter, preferably a capillary bore 39, which passes through the plunger 35, designed as an adapter, in the longitudinal direction and opens at the top in a conical sealing region 41. Sealed connections to a pump or a pipetting needle may be made in this region.

Between the capillary bore 39 and the conical sealing region 41 an additional cylindrical section 43 is preferably provided which may also be used as a guide.

On the end of the plunger 35 opposite from the conical sealing region 41 a receptacle 45 is provided, into which a filter disk may be inserted.

It is seen that the lower edge of the base body 37 of the plunger 35 has a downwardly conically expanding wall section 47 which projects beyond the circumferential surface 49 and serves as a seal. Thus, when the plunger 35 used as an adapter is introduced into a column body 1 this wall section 47 makes sealing contact with the inner wall of the column body 1, and preferably has a flexible design in order to form a sealing lip.

At its upper edge the plunger 35 may be provided with an annular bead 51 which is used as a stop and which, on account of the annular bead 51 resting against the upper edge of the column body 1, ensures a defined end position when the plunger 35 is inserted into the column body 1.

Figure 10:
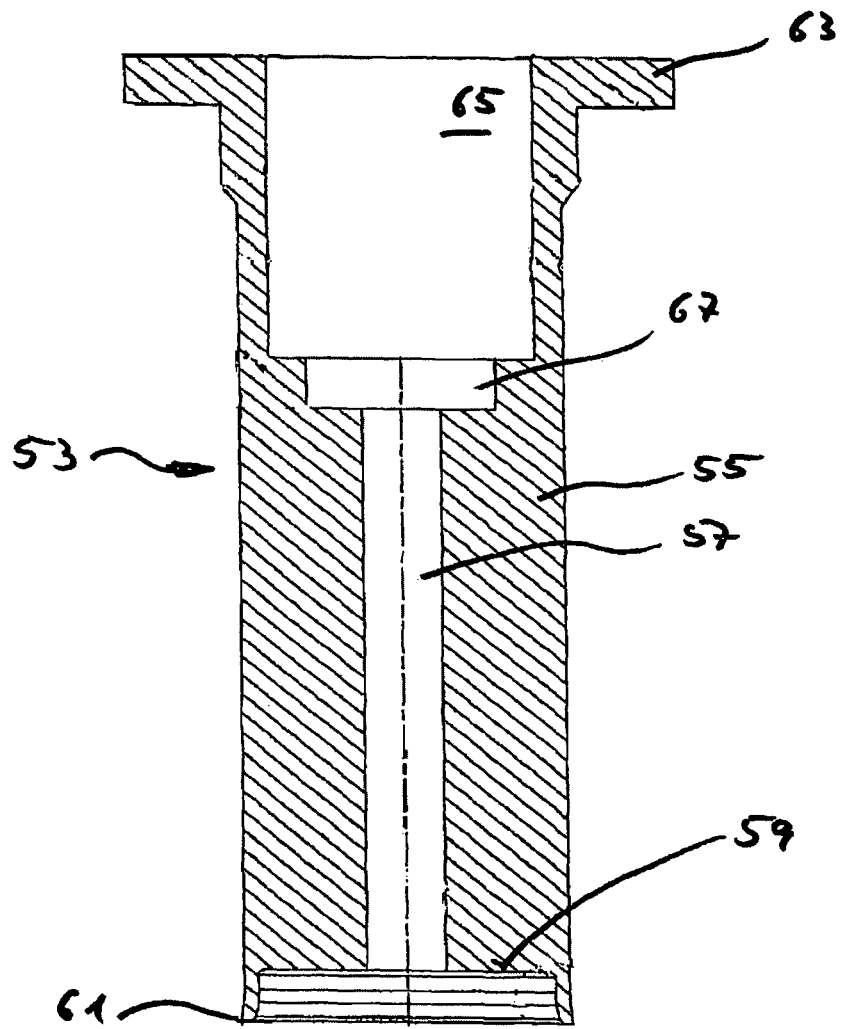
FIG. 10 is a cross-sectional view of another plunger in accordance with the present teachings.

FIG. 10 shows a modified exemplary embodiment of a plunger 53 provided as an adapter, having a specialized design such that a sample plate equipped with chromatographic columns of the type involved here may be operated automatically, preferably by robotic systems.

The plunger 53 has a base body 55 through which a channel opening, preferably a capillary bore 57, passes, which opens at the bottom into a receptacle 59 into which a filter plate may be inserted.

Here as well, the bottommost wall section 61 expands conically downward and preferably has an elastic design, as in the exemplary embodiment according to FIG. 9, for achieving a seal.

The upper end of the plunger 53 is enclosed by an annular bead 63, which is used as a stop when the plunger 53 is inserted into a column body 1 and specifies a defined position. In the upper region of the plunger 53 facing the annular bead 63 a cylindrical recess 65 is provided which may be used as a guide. An additional section may be provided farther down in the immediately adjacent transition region to the capillary bore 57, and has a smaller inner diameter than the recess 65 and likewise may be used as a guide.

Figure 11:
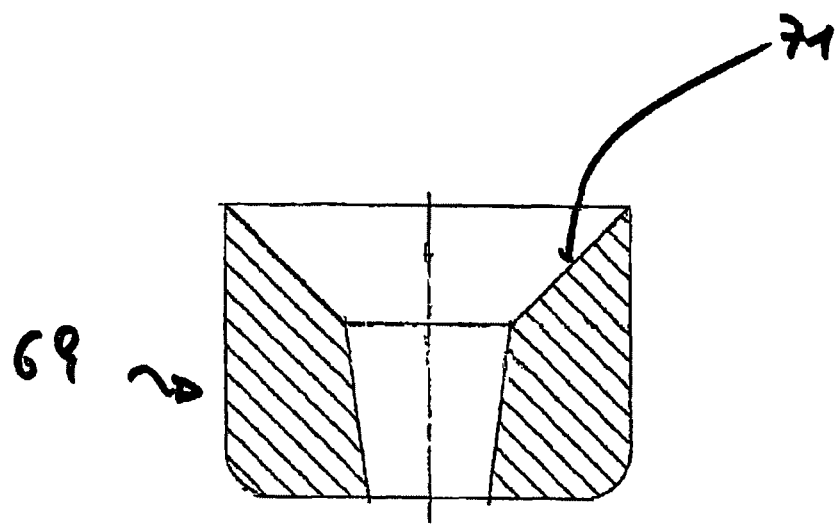
FIG. 11 is a cross-sectional view of an adapter in accordance with the present teachings.

An adapter 69, illustrated in the longitudinal section in FIG. 11, which facilitates automatic operation of the chromatographic column may be inserted into the cylindrical recess 65 in the plunger 53. The outer diameter thereof may be modified to the inner diameter of the recess 65 in such a way that after insertion the adapter is securely clamped in place at that location.

At its upper end the adapter 69 may be provided with a conical sealing region 71 at which automatic filling devices, for example pipetting needles, may make sealing contact, at least in places.

Figure 12:
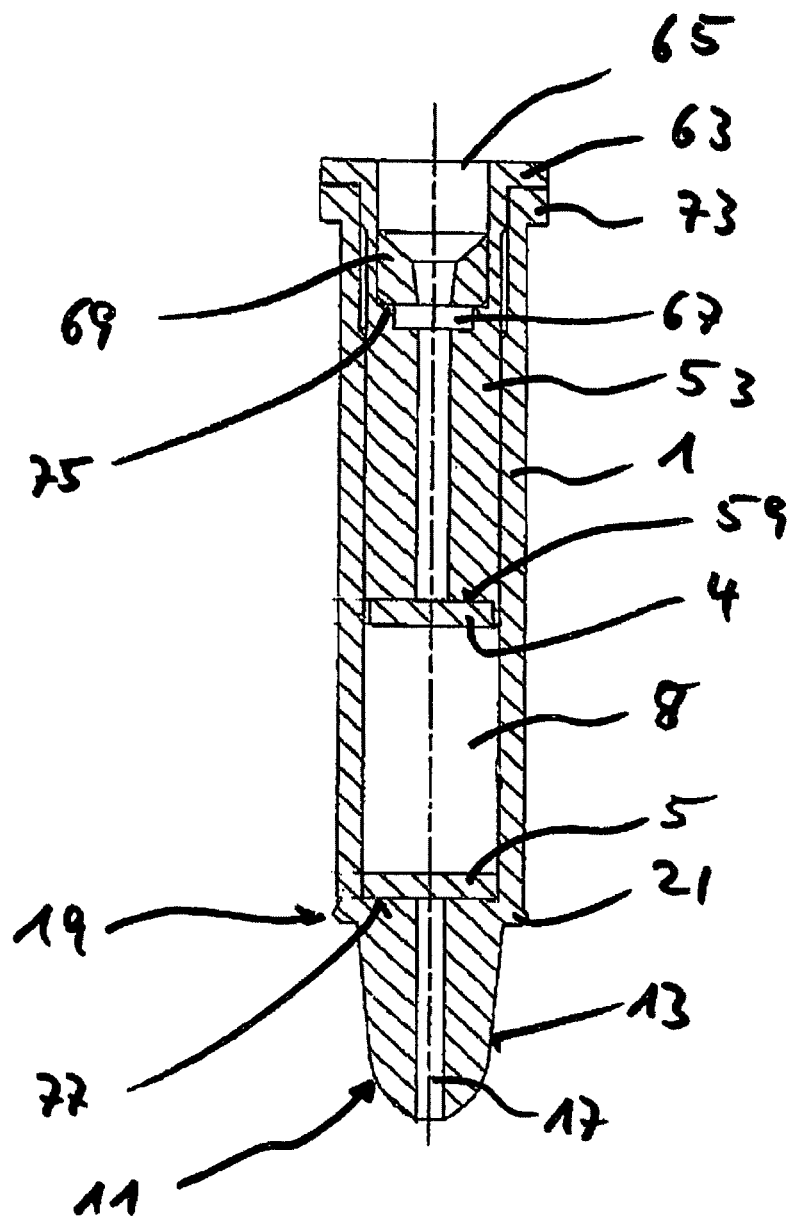
FIG. 12 is a cross-sectional view of a chromatography column constructed to include the column body of FIG. 6, the plunger of FIG. 10 and the adapter of FIG. 11.

FIG. 12 shows in the longitudinal section a chromatographic column in the assembled state, which includes the elements illustrated in FIGS. 6, 10, and 11. Identical parts are provided with the same reference numerals, so that reference may be made to the explanations for the preceding figures.

The chromatographic column has a column body 1 into which the adapter 53 is inserted. The annular bead 63 rests against a projection, preferably an annular bead 73 of the column body 1, which serves as a stop, resulting in a defined longitudinal position of the plunger 53, used as an adapter, inside the column body 1, thus also providing a defined compression of the chromatographic material.

The adapter 69 illustrated in FIG. 11 is inserted into the upper cylindrical recess 65 of the plunger 63, the adapter being supported in the transition region between the cylindrical recess 65 and the section 67, in this case designed as a shoulder 75. An upper filter plate 4 accommodated in the recess 59 in the plunger 53 is inserted into the lower end of the plunger 63. The lower filter plate 5, which rests on the upper boundary surface 77 of the attachment 11, may be seen at the lower end of the gel chamber 8.

Figure 13:
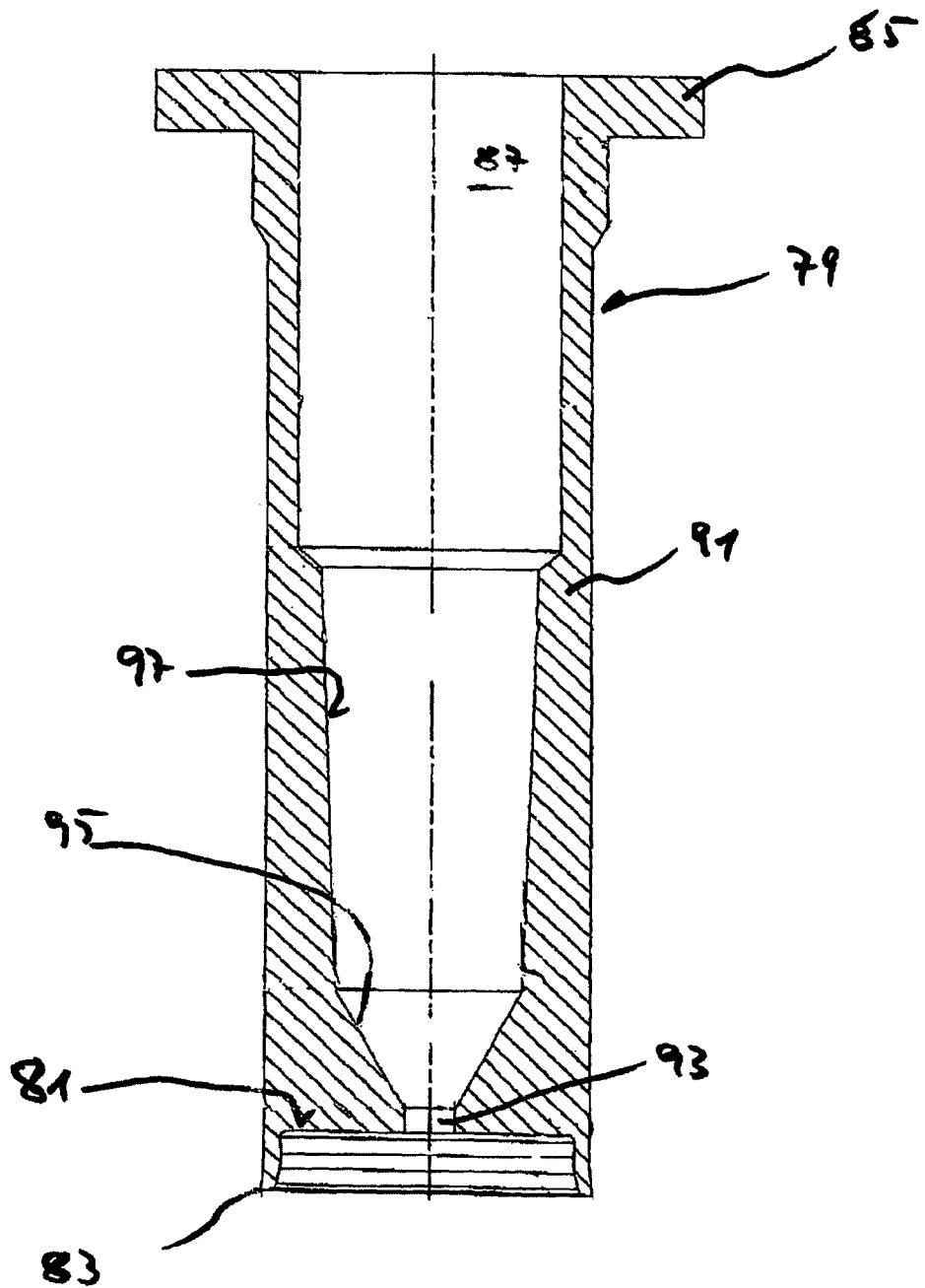
FIG. 13 is a cross-sectional view of another plunger in accordance with the present teachings.

A plunger 79 having the same basic design as the plunger 53, and used as an adapter, illustrated in the longitudinal section in FIG. 13, is particularly preferred. At its lower end the plunger has a receptacle 81 for a filter plate, in addition to a conical wall region 83 at its lower edge which preferably is elastically resilient and serves as a seal. Lastly, at its upper end the plunger has an annular bead 85 which functions as a stop when the plunger 79 is inserted into a column body 1.

The interior 87 of the plunger 79 has a specialized design which is used for accommodating a pipetting tip, which is much less expensive than a conventional pipetting needle. At its lower end the base body 89 of the plunger 79 has a borehole 91, directly in front of the receptacle 81, above which a conical sealing region 93 is present. The pipetting tip rests in a sealing manner against the sealing region when a medium is to be introduced through the pipetting tip into the gel chamber situated below the plunger 79. Above and slightly behind the conical sealing region 93, which opens upwardly in the direction of the annular bead 85, there is preferably another upwardly opening conical region 95 which may support a pipetting tip. The uppermost region of the interior 87 may have a cylindrical design. Overall, the interior 87 should be designed so that it may be used for accommodating, supporting, and providing a sealing enclosure for conventional pipetting tips.

The plunger 79 is characterized in that chromatographic columns may be operated in a relatively economical manner when the plunger is used. Pipetting needles are subjected to wear when used, due to the fact that they have a coating which acts as a sliding layer and is worn off during use. Therefore, pipetting needles must generally be replaced after a certain number of uses. The manufacture of such needles is fairly complex and therefore expensive, in particular on account of the outer coating.

In contrast, pipetting tips may be manufactured in large numbers at relatively low cost. As a result of the design of the plunger 79 as an adapter for such pipetting tips, use of chromatographic columns having column bodies 1 in which a plunger 70 is incorporated is much more economical.

It has been shown that all exemplary embodiments share the common feature that a plunger is used which may be inserted into a column body 1 over a defined path. The plunger may be designed as a sample chamber or adapter which allows the various uses and applications of a chromatographic column described herein.

When a plunger is used in conjunction with chromatographic columns of the type involved here, the plunger may also preferably be designed so that it is adaptable to different inner diameters of column bodies. For example, the plunger may have a base body which can be adapted to various uses as described above. It may be designed as a sample chamber, or also as an adapter. This base body may be used with sleeves of various thicknesses, or with a number of different sleeves which may be placed concentrically one inside the other. The at least one sleeve encloses the base body of the plunger, and has an outer diameter which is adapted to the inner diameter of a column body, and at that location it is sealed and also rests stationarily so that it exhibits the clamping effect described above. When the plunger, with or without a sleeve, is inserted into a corresponding column body it remains in the inserted position in such a way that is not displaced by internal pressure produced by the chromatographic material, thereby maintaining the desired compression pressure on the material.

TABLE 1

Plate numbers and asymmetry factors of the elution profiles for the pseudochromatograms of a selection of 20 of 96 similar minicolumns.

| Column No. | Elution volume[1] μL | Half-value width[2] μL | Bed height cm | Plate number per meter N/m | Plate number per cm N/cm | Section B at 10% of peak height mm | Section A at 10% of peak height Mm | Asymmetry factor (B/A) |
|---|---|---|---|---|---|---|---|---|
| 1 | 208.0 | 100.0 | 1.1 | 2179 | 22 | 35.0 | 22.0 | 1.6 |
| 5 | 216.0 | 93.0 | 1.1 | 2717 | 27 | 27.0 | 23.5 | 1.1 |
| 10 | 217.0 | 96.0 | 1.1 | 2573 | 26 | 29.5 | 25.5 | 1.2 |
| 15 | 217.4 | 99.4 | 1.1 | 2409 | 24 | 26.5 | 25.0 | 1.1 |
| 20 | 218.9 | 94.0 | 1.1 | 2731 | 27 | 25.0 | 24.0 | 1.0 |
| 25 | 216.7 | 93.0 | 1.1 | 2734 | 27 | 29.5 | 25.0 | 1.2 |
| 30 | 215.8 | 93.0 | 1.1 | 2712 | 27 | 31.0 | 24.2 | 1.3 |
| 35 | 211.0 | 93.0 | 1.1 | 2592 | 26 | 27.8 | 22.3 | 1.2 |
| 40 | 206.0 | 94.6 | 1.1 | 2388 | 24 | 31.0 | 22.5 | 1.4 |
| 45 | 215.8 | 100.0 | 1.1 | 2345 | 23 | 27.5 | 26.0 | 1.1 |
| 50 | 213.2 | 91.5 | 1.1 | 2734 | 27 | 30.5 | 24.5 | 1.2 |
| 55 | 209.5 | 104.0 | 1.1 | 2044 | 20 | 35.0 | 25.0 | 1.4 |
| 60 | 215.8 | 101.0 | 1.1 | 2299 | 23 | 27.0 | 25.5 | 1.1 |
| 65 | 215.1 | 102.5 | 1.1 | 2218 | 22 | 31.5 | 25.0 | 1.3 |
| 70 | 213.5 | 104.0 | 1.1 | 2122 | 21 | 35.5 | 26.0 | 1.4 |
| 75 | 214.2 | 103.2 | 1.1 | 2170 | 22 | 34.5 | 25.5 | 1.4 |
| 80 | 212.6 | 96.2 | 1.1 | 2460 | 25 | 30.0 | 24.0 | 1.3 |
| 85 | 214.8 | 100.9 | 1.1 | 2282 | 23 | 27.0 | 26.0 | 1.0 |
| 90 | 215.8 | 100.9 | 1.1 | 2304 | 23 | 27.3 | 26.8 | 1.0 |
| 95 | 214.2 | 100.9 | 1.1 | 2270 | 23 | 27.5 | 25.0 | 1.1 |
| Mean value | 214.1 | 98.1 | | 2414 | 24 | | | 1.2 |
| STDDEV[3] | 3.2 | 4.1 | | 222 | 2.2 | | | 0.15 |

[1] The elution volume is assigned to the maximum of the elution profile determined by computer.
[2] The half-value width corresponds to the width of the elution profile at a height corresponding to 50% of the distance between the baseline and the maximum height of the profile.
[3] The standard deviations (STDDEV) were calculated according to the following formula:

$$STDDEV = \sqrt{\frac{\sum (x - \bar{x})^2}{n}}$$

where x is the individual measured value, $\bar{x}$ is the mean value, and n is the number of measured values.

The invention claimed is:

1. A chromatographic column comprising:
 a generally cylindrical column body for enclosing chromatographic material in a defined compressed state within a gel chamber having an inner diameter, the column body having a discharge opening, an upper edge, and a convexly curved outer surface at a lower end thereof;
 a plunger having an outer diameter larger than the inner diameter of the gel chamber and inserted in the column body, the plunger designed as one of a sample chamber and an adapter;
 upper and lower filter plates positioned at a specified distance from one another when the plunger is inserted a predetermined distance into the column body and engages the upper edge of the column body, the lower filter plate being held in position by resting on a projection and the upper filter plate integrated into a lower portion of the plunger and movable with the plunger to define the gel chamber within the column body when the plunger is inserted the predetermined distance.

2. The chromatographic column according to claim 1, wherein the projection has a width between 0.3 mm and a value which leaves a discharge opening of at least 1 mm in diameter in a center of the column.

3. The chromatographic column according to claim 1, wherein contact between the plunger and the upper edge of the column body limits a depth to which the plunger may be inserted into the column body and defines the predetermined distance.

4. The chromatographic column according to claim 1, wherein an opening is provided in the upper filter plate at a lower end of the plunger for passage of liquids from the sample chamber, the diameter of the opening being between 1 mm and up to 2 mm smaller than the inner diameter of the column body.

5. The chromatographic column according to claim 1, wherein a lower edge of the plunger is designed as a sealing lip which ensures a complete and permanent seal between the sample chamber and an inner wall of the column body.

6. The chromatographic column according to claim 5, wherein a lower part of the plunger is designed as a filter holder in such a way that the inserted filter plate comes to rest at a level of the sealing lip.

7. The chromatographic column according to claim 6, wherein the inserted filter plate comes to rest at a distance of up to 5 mm, preferably up to 3 mm, and in particular up to 1 mm, above the sealing lip.

8. The chromatographic column according to claim 1, wherein an inner diameter of the column body is between approximately 3 mm to approximately 16 mm.

9. The chromatographic column according to claim 1, wherein an inner diameter of the column body is approximately 8 mm to approximately 20 mm, and/or wherein the inserted filter plates have a thickness of approximately 0.4 to approximately 3 mm.

10. The chromatographic column according to claim 1, wherein the chromatographic column is loaded with quasi-elastic packings of chromatographic media compressed in a defined manner.

11. The chromatographic column according to claim 1, wherein the plunger at its end situated inside the column body has a receptacle into which a filter plate may be inserted.

12. The chromatographic column according to claim 1, wherein the plunger at its upper end has a stop.

13. The chromatographic column according to claim 1, wherein the plunger at its upper end has a conical sealing region.

14. The chromatographic column according to claim 1, wherein the plunger has a cavity for accommodating an adapter.

15. The chromatographic column according to claim 1, wherein a device provided at an upper end of the chromatographic column is adapted to provide at defined pressure force exerted on the plunger inserted into the column body.

16. The chromatographic column according to claim 1, wherein the chromatographic column has a column body with an attachment having a curved, outer surface.

17. The chromatographic column according to claim 1, wherein the column body is provided with a locking device for anchoring in a sample plate.

18. The chromatographic column according to claim 1, wherein the plunger is designed as a sample chamber.

19. The chromatographic column according to claim 1, wherein the plunger is designed as an adapter for accommodating a pipetting tip.

20. The chromatographic column according to claim 1, wherein the plunger is designed as an adapter having a base body and at least one sleeve enclosing the base body, so that a peripheral surface may be adapted to column bodies having different inner diameters.

21. The chromatographic column according to claim 1, wherein the outer diameter of the plunger is 0.02 to 0.1 mm larger than the inner diameter of the gel chamber.

22. The chromatographic column according to claim 1, wherein the outer diameter of the plunger is 0.03 to 0.05 mm larger than the inner diameter of the gel chamber.

23. A chromatographic column comprising:
    a generally cylindrical column body having a discharge opening and a convexly curved outer surface at a distal end, the generally cylindrical column body defining a hollow interior having a proximal portion and a central portion disposed between the proximal portion and the discharge opening, the proximal portion having a first diameter, the central portion having a second diameter, the first diameter being greater than the second diameter;
    a plunger inserted into the proximal portion of the hollow interior of the generally cylindrical column body, the plunger having an outer diameter greater than the second diameter; and
    upper and lower filter plates disposed in the hollow interior of the generally cylindrical column body, the upper and lower filter plates at upper and lower ends of the central portion, respectively, a distance between the upper and lower filter plates defining a gel cavity for enclosing a chromatographic material in a compressed state with the upper filter plate carried by the plunger and movable with the plunger relative to the lower filter plate.

24. The chromatographic column according to claim 23, wherein the upper filter plate is integrated into a lower portion of the plunger.

25. The chromatographic column according to claim 23, wherein the outer diameter of the plunger is 0.02 to 0.1 mm larger than the second diameter.

26. The chromatographic column according to claim 23, wherein the outer diameter of the plunger is 0.03 to 0.05 mm larger than the second diameter.

* * * * *